(12) United States Patent
Huang

(10) Patent No.: US 11,684,513 B2
(45) Date of Patent: Jun. 27, 2023

(54) OPHTHALMIC LASER APPARATUS

(71) Applicant: EXCELSIUS MEDICAL CO., LTD., Tainan (TW)

(72) Inventor: Cheng-Hao Huang, Tainan (TW)

(73) Assignee: Excelsius Medical Co., Ltd., Tainan (TW)

( * ) Notice: Subject to any disclaimer, the term of this patent is extended or adjusted under 35 U.S.C. 154(b) by 0 days.

(21) Appl. No.: 17/097,196

(22) Filed: Nov. 13, 2020

(65) Prior Publication Data

US 2022/0151832 A1    May 19, 2022

(51) Int. Cl.
 *A61F 9/008* (2006.01)
(52) U.S. Cl.
 CPC .............. *A61F 9/00814* (2013.01); *A61F 2009/00846* (2013.01); *A61F 2009/00887* (2013.01); *A61F 2009/00891* (2013.01)
(58) Field of Classification Search
 CPC ............................................ A61F 9/008–009
 See application file for complete search history.

(56) References Cited

U.S. PATENT DOCUMENTS

| | | | | |
|---|---|---|---|---|
| 3,703,176 A | * | 11/1972 | Vassiliadis | A61F 9/00821 606/3 |
| 3,720,213 A | * | 3/1973 | Hobart | A61F 9/00821 606/40 |
| 4,309,998 A | * | 1/1982 | Aron nee Rosa | A61F 9/008 606/3 |
| 5,098,426 A | * | 3/1992 | Sklar | A61F 9/008 606/5 |
| 2003/0004502 A1 | * | 1/2003 | Clapham | A61F 9/00804 606/5 |
| 2008/0278687 A1 | * | 11/2008 | Somani | A61B 3/0083 351/208 |
| 2009/0079939 A1 | | 3/2009 | Mimura | |
| 2012/0316544 A1 | * | 12/2012 | Horvath | A61F 9/00745 606/6 |
| 2014/0114296 A1 | | 4/2014 | Woodley et al. | |
| 2019/0231594 A1 | * | 8/2019 | Abraham | A61F 9/00802 |

FOREIGN PATENT DOCUMENTS

| | | |
|---|---|---|
| JP | 2020081792 A | 6/2020 |
| WO | 2020008323 A1 | 1/2020 |
| WO | 2020183342 A1 | 9/2020 |

* cited by examiner

*Primary Examiner* — Nathan J Jenness
(74) *Attorney, Agent, or Firm* — Rosenberg, Klein & Lee

(57) ABSTRACT

An ophthalmic laser apparatus comprises a laser light source; a light guide device, configured to guide a laser beam generated from the laser light source; a support bracket, configured to support a patient's head for the patient's eye to be perpendicular to a horizontal plane; a positioning device to acquire data related to a position of the patient's eye; a laser beam projector, the laser beam projector being movable to be aligned with the patient's eye and projecting the laser beam from the light guide device; a moving stand, configured to move the positioning device and the laser beam projector along an X direction, a Y direction, and/or a Z direction; and a controller, configured to control the laser light source to irradiate the laser beam and to control the laser beam projector to project the laser beam toward the patient's eye.

10 Claims, 5 Drawing Sheets

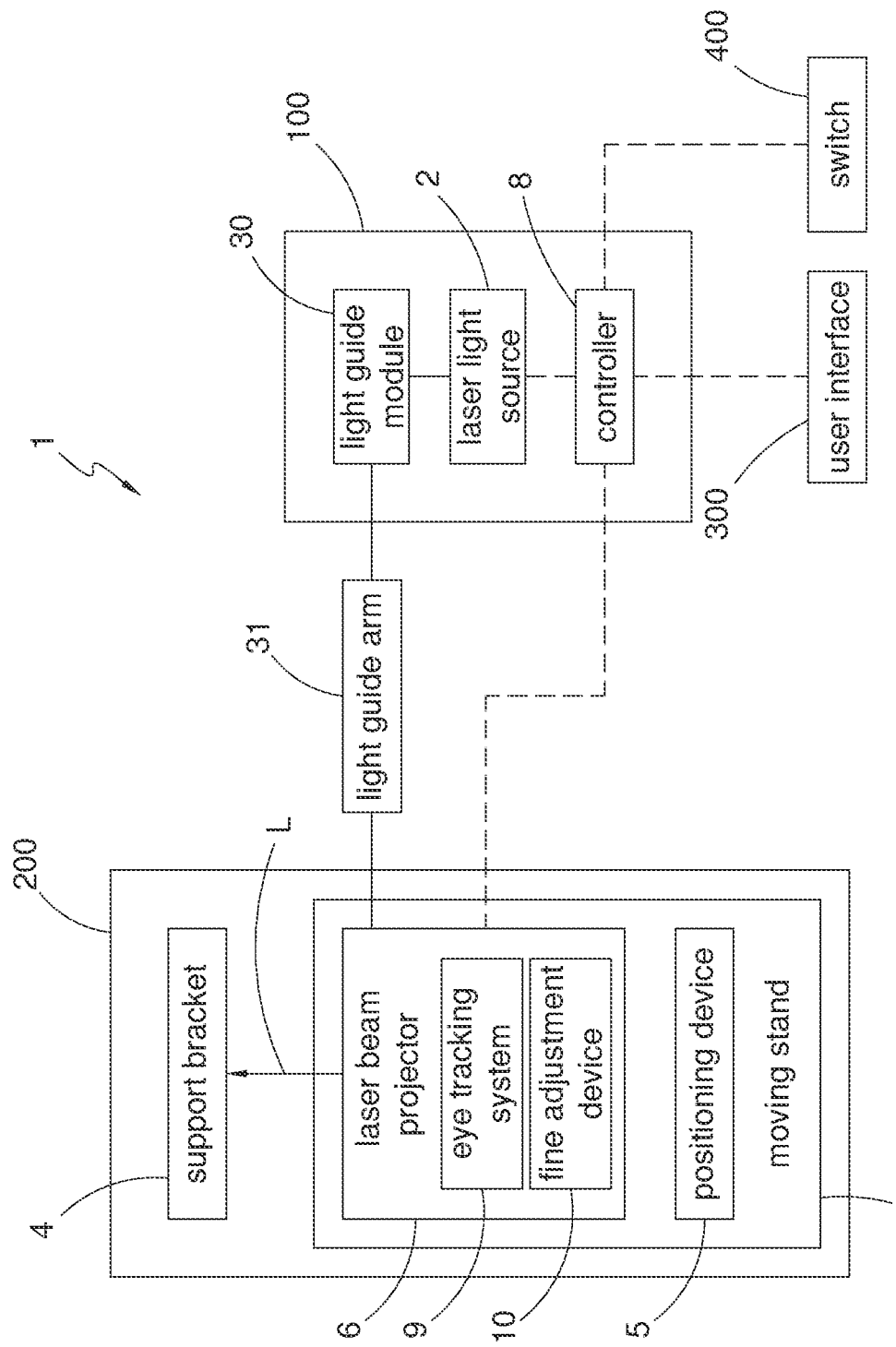
F I G . 3

OPHTHALMIC LASER APPARATUS

FIELD OF THE INVENTION

The present invention relates to an ophthalmic laser apparatus.

BACKGROUND OF THE INVENTION

In the structure of the eye, about two-thirds of the diopter is determined by the curvature of the front of the cornea. Therefore, the refractive error of the eye can be significantly improved or eliminated by changing the shape of the cornea. The cornea is a multi-layer film. The front and back of the cornea are almost concentric. The cornea has a central thickness of about 0.5 to 0.6 mm and an edge thickness of about 0.6 to 0.8 mm. The multi-layer structure of the cornea from the front to the back includes five layers, namely, the epithelium, Bowman's layer, the stroma, Descemet's membrane, and the endothelium. The central thickness of the epithelium is about 70 μm, and the thickness of Bowman's layer is about 12 μm. The thickness of the stroma accounts for about 90% of the total thickness of the cornea (about 500 μm), and it is mainly composed of regularly arranged collagen fibers and interconnected corneal cells. The endothelium is composed of a layer of hexagonal flat cells.

Based on the corneal structure described above, since the stroma of the cornea has a sufficient thickness, for the purpose of correction, the front part of the stroma can be removed to change its contour, thereby changing the diopter of the eye while remaining most of the tissue of the stroma.

Various lasers are widely used in ophthalmic surgery, for example, glaucoma, cataract, refractive eye surgery, etc. For example, ultraviolet (UV) lasers are used in refractive eye surgery (or Laser-Assisted in Situ Keratomileusis) Ultraviolet lasers include 193 nm excimer lasers, fifth harmonic (213 nm) neodymium crystal lasers (Neodymium-Uttrium Aluminum Garnet; Nd-YAG laser) and so on. Specifically, these ultraviolet lasers are widely used in Photorefractive keratectomy (PRK) and Laser-Assisted In Situ Keratomileusis (LASIK), etc. They all use laser beam to ablate the corneal tissue to change its curvature, thereby changing the diopter of the eye (vision correction).

In general, conventional ophthalmic laser apparatus used to perform LASIK has a similar design, aligning the visual axis of the patient's eye with the laser beam by moving the operating table where the patient is located. Specifically, the patient will lie on an operating table that can be precisely moved along the X axis, Y axis and Z axis. The patient (that is, the surface of the cornea) will be moved along with the operating table until the surface of the cornea reaches the focal point of the microscope in the ophthalmic laser apparatus, and then the laser beam transmission path is set. In the ophthalmic laser apparatus, because the main cabinet provided with the laser light source is large in size and cannot be moved conveniently, the laser beam is usually transmitted through an optical system. After passing through the optical system, the laser beam is turned downward under the microscope to align the optical axis of the microscope. During the use of such ophthalmic laser apparatus, in order to align the visual axis of the patient's eye with the laser beam, the operating table on which the patient is located needs to be moved and adjusted again and again. In such a situation, because the operating table is large in size, it is easy to cause inconvenience to the operator (for example, a doctor or an operating assistant).

On the other hand, in ophthalmic laser surgery, the patient needs to undergo a series of related examinations in a sitting posture before surgery, and then move to the operating table to have ophthalmic laser surgery in a lying posture. In such a case, the various parameters of the patient's eye will be slightly different in a sitting posture and in a lying posture, for example, the difference in the angle of astigmatism caused by the different rotation angles of the eye in a sitting posture and in a lying posture. Such a difference will make the operations of the surgery not precise enough, which will be a serious problem for ophthalmic laser surgery that requires high precision.

SUMMARY OF THE INVENTION

The primary object of the present invention is to provide an ophthalmic laser apparatus. The patient can receive the laser beam from the ophthalmic laser apparatus in a sitting posture for performing ophthalmic laser surgery. The alignment between the ophthalmic laser apparatus and the patient's eye is done by moving the ophthalmic laser apparatus. There is no need to move the position of the patient relative to the ophthalmic laser apparatus.

The present invention provides an ophthalmic laser apparatus, comprising a laser light source, configured to generate a laser beam; a light guide device, configured to guide the laser beam generated from the laser light source; a support bracket, configured to support a patient's head for an exposed surface of the patient's eye to be perpendicular to a horizontal plane; a positioning device, configured to position a position of the patient's eye supported on the support bracket; a laser beam projector, the laser beam projector being movable to be aligned on the support bracket; a laser beam projector, the laser beam projector being movable to be aligned with the patient's eye supported on the support bracket based on a positioning result of the positioning device, the laser beam from the light guide device being projected toward the patient's eye through the laser beam projector; a moving stand, the positioning device and the laser beam projector being arranged on the moving stand, the moving stand being configured to move the positioning device and the laser beam projector along an X direction, a Y direction, and/or a Z direction; and a controller, configured to control the laser light source to irradiate the laser beam and to control the laser beam projector to project the laser beam toward the patient's eye.

With the ophthalmic laser apparatus of the present invention, since the support bracket is configured to keep the exposed surface of the patient's eye perpendicular to the horizontal plane, in addition to receiving related examinations before surgery in a sitting posture, the patient can receive the laser beam projected from the laser beam projector in a sitting posture to perform ophthalmic laser surgery. In this way, there will not be much difference in the condition of the patient's eyes when undergoing related examinations before surgery and when a laser beam is projected for ophthalmic laser surgery, so that the more precise operation of ophthalmic laser surgery can be performed. Therefore, the ophthalmic laser apparatus is particularly suitable for ophthalmic laser surgery that requires high precision.

On the other hand, with the ophthalmic laser apparatus of the present invention, the alignment between the patient's eye and the ophthalmic laser apparatus is done by moving the ophthalmic laser apparatus. There is no need to move the position of the patient relative to the ophthalmic laser apparatus, that is, there is no need for the operator to move the operating table where the patient is located. Therefore, the ophthalmic laser apparatus according to the present invention is more convenient in operation and use.

BRIEF DESCRIPTION OF THE DRAWINGS

FIG. 3 is a block diagram of the ophthalmic laser apparatus according to the embodiment of the present invention.

DETAILED DESCRIPTION OF THE PREFERRED EMBODIMENTS

Figure 1:
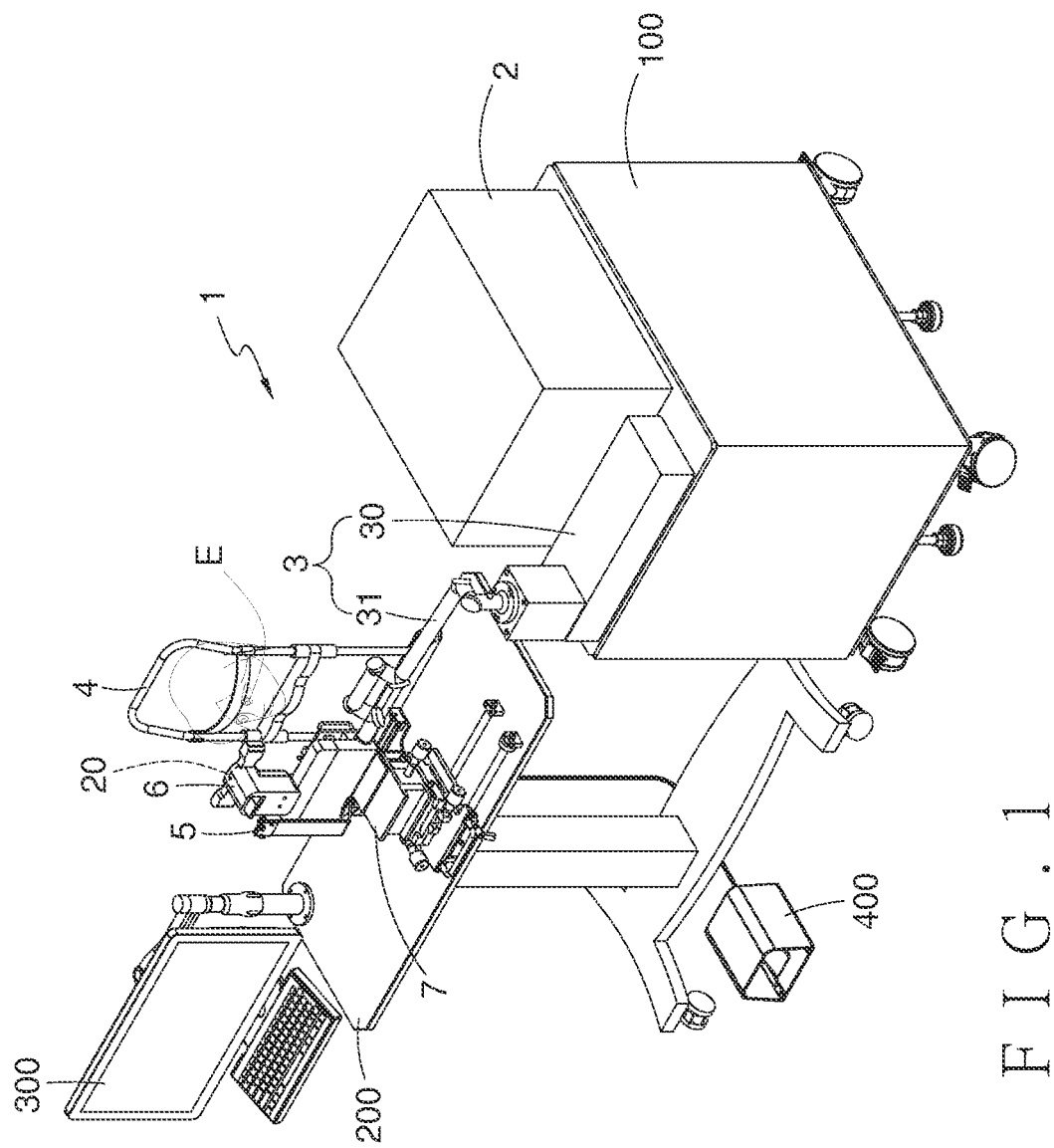
FIG. 1 is a perspective view of the ophthalmic laser apparatus according to an embodiment of the present invention.
Figure 2:
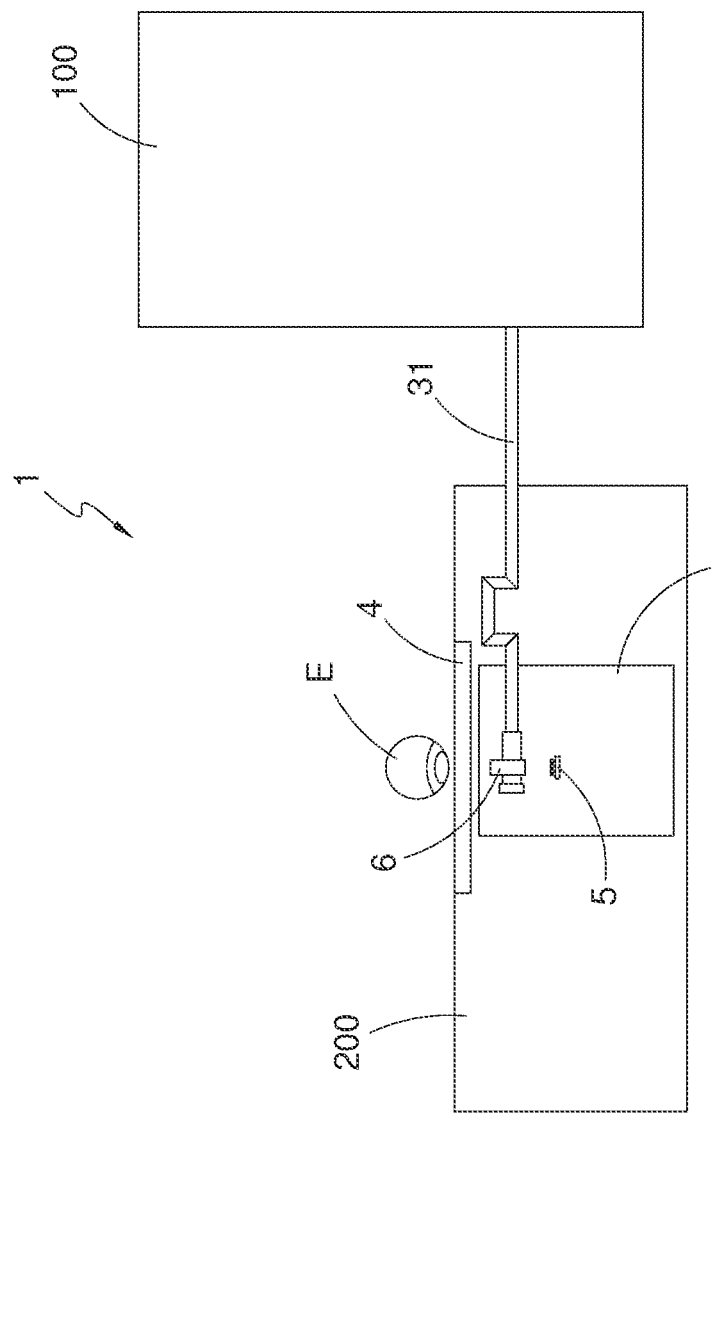
FIG. 2 is a top view of the ophthalmic laser apparatus according to the embodiment of the present invention (some elements are omitted in the figure)

FIGS. 1 to 3 show an ophthalmic laser apparatus 1 according to an embodiment of the present invention. FIG. 1 is a perspective view of the ophthalmic laser apparatus 1 according to an embodiment of the present invention. The X direction and Y direction is a direction perpendicular to the horizontal plane. FIG. 2 is a top view of the ophthalmic laser apparatus according to the embodiment of the present invention (some elements are omitted in the figure). FIG. 3 is a block diagram of the ophthalmic laser apparatus 1 according to the embodiment of the present invention.

The ophthalmic laser apparatus 1 of the present invention comprises a laser light source 2, a light guide device 3 having a light guide module 30 and a light guide arm 31, a support bracket 4, a moving stand 7, a positioning device 5 and a laser beam projector 6 arranged on the moving stand 7, and a controller 8.

The laser light source 2 is configured to generate a laser beam L, for example, an excimer laser beam. With the excimer laser beam, ophthalmic laser surgery can be performed on the eye E of a patient, for example, LASIK surgery.

The light guide module 30 and the light guide arm 31 of the light guide device 3 are configured to guide the laser beam generated from the laser light source 2. The laser beam is guided to the laser beam projector 6 and then travels toward the eye E of the patient.

Figure 5:
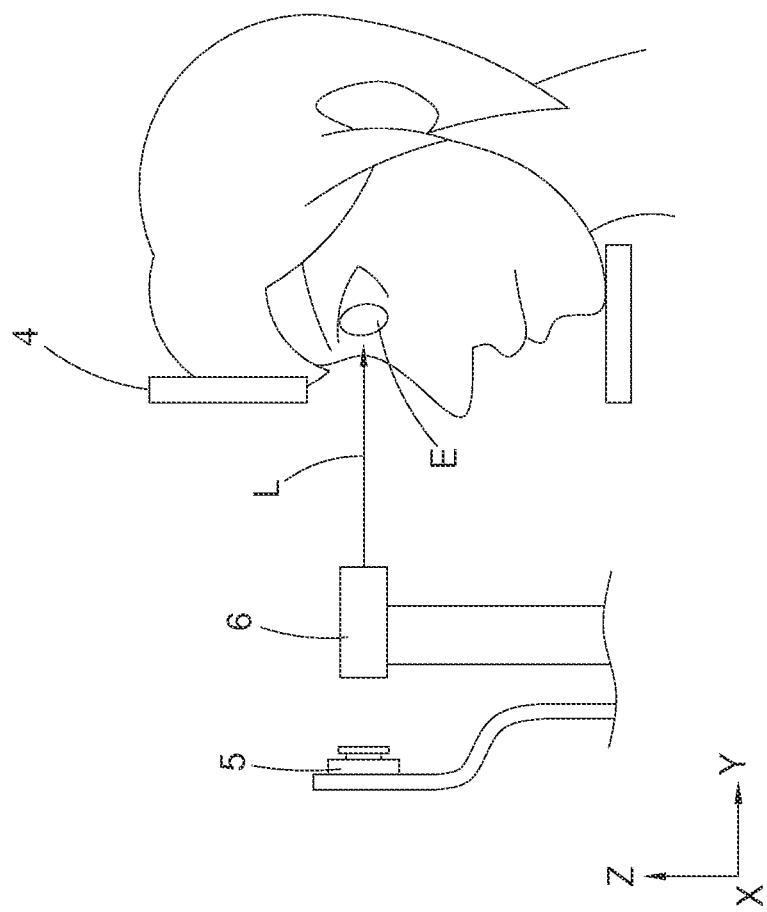
FIG. 5 is a schematic view of the ophthalmic laser apparatus according to the embodiment of the present invention when in use.

The support bracket 4 is configured to support the head of the patient so that the exposed surface of the eye E of the patient is perpendicular to the horizontal plane. In other words, the patient will undergo the ophthalmic laser surgery performed by the laser beam L from the laser beam projector 6 in a sitting posture, as shown in FIG. 5. Preferably, the support bracket 4 is adjustable in height along the Z direction, so as to meet the needs of different patients.

The moving stand 7 is configured to move the positioning device 5 and the laser beam projector 6 that are disposed on the moving stand 7 along the X direction, the Y direction, and/or the Z direction.

Through the moving stand 7, the positioning device 5 can be moved for acquiring the position of the eye E of the patient supported on the support racket 4, for example, the position of the left or right eye of the patient. The positioning device 5 generates a positioning result based on the position of the patient's eye. In the embodiment of the present invention, the positioning device 5 is a camera, and is configured to move along the X direction, the Y direction and/or the Z direction when the operator manually operates the moving stand 7, but not limited thereto. For example, according to the accuracy requirements of different surgeries, the positioning device 5 may be a microscope, etc., and the moving stand 7 may be an electric moving stand. The electric moving stand enables the positioning device to move electrically under the control of the controller 8.

Similarly, through the moving stand 7, the laser beam projector 6 can be moved based on the positioning result of the positioning device 5 to align the laser beam with the eye E of the patient supported on the support bracket 4 (for example, the left eye or right eye of the patient. This positioning can be referred to as the primary positioning of the laser beam projector 6.

It should be noted that, in the ophthalmic laser apparatus 1 according to the present invention, the laser beam projector 6 further includes an eye tracking system 9 and a fine adjustment device 10. The eye tracking system 9 is configured to track the position of the patient's eye E. As the position of the patient's eye E may change during the procedure, the tracking system 9 produces a repositioning result based on the positional change of the patient's eye. The fine adjustment device 10 is operatively coupled to the eye tracking system 9 and is configured to fine adjust the position of the laser beam projector 6 according to the repositioning result of the eye tracking system 9, so that the laser beam projector 6 can be aligned with the patient's eye E accurately. This positioning is referred to as the fine positioning of the laser beam projector 6. Next, the laser beam L from the light guide device 3 is projected to the patient's eye E through the laser beam projector 6 to perform ophthalmic laser surgery, for example, LASIK surgery.

The movement of the positioning device 5 and the laser beam projector 6 relative to the patient's eye E will be described in further detail below, and will not be repeated here.

Preferably, the ophthalmic laser apparatus 1 according to the present invention further includes a condenser 20. The condenser 20 is arranged on one side of the laser beam projector 6, facing the patient's eye E, so that the laser beam L projected by the laser beam projector 6 toward the patient's eye E can be focused on the target position of the patient's eye E.

The controller 8 is configured to control the various components of the ophthalmic laser apparatus 1. Specifically, the controller 8 is configured to control the laser light source 2 to irradiate the laser beam L and to control the laser beam projector 6 to project the laser beam L toward the patient's eye E.

In addition, the ophthalmic laser apparatus 1 further includes a cabinet 100 and an operating platform 200. The laser light source 2, the light guide module 30 of the light guide device 3, and the controller 8 are arranged on the cabinet 100. The support bracket 4, the moving stand 7, the positioning device 5 and the laser beam projector 6 on the moving stand 7 are arranged on the operating platform 200. In other words, the cabinet 100 and the operating platform 200 are connected through the light guide arm 31 that is connected between the light guide module 30 on the cabinet 100 and the laser beam projector 6 on the operating platform 200.

In order to conveniently adjust the position of the ophthalmic laser apparatus 1 to meet the needs of the operator better, both the cabinet 100 and the operating platform 200 are designed to be movable on the ground. For example, the cabinet 100 and the operating platform 200 have their respective wheels, so as to move on the ground. On the other hand, the maximum length (or width) of the cabinet 100 is only 70 cm, so that it can be moved to enter an elevator smoothly. This is more advantageous for the transportation of the ophthalmic laser apparatus 1 according to the present invention.

Figure 4A:
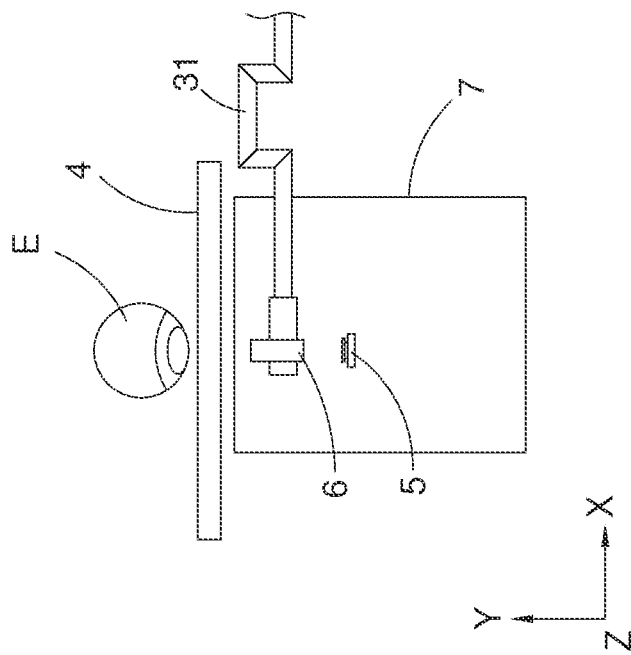
FIG. 4A is a first schematic view showing the movement of the positioning device and the laser beam projector of the ophthalmic laser apparatus relative to the patient's eye according to the embodiment of the present invention.
Figure 4B:
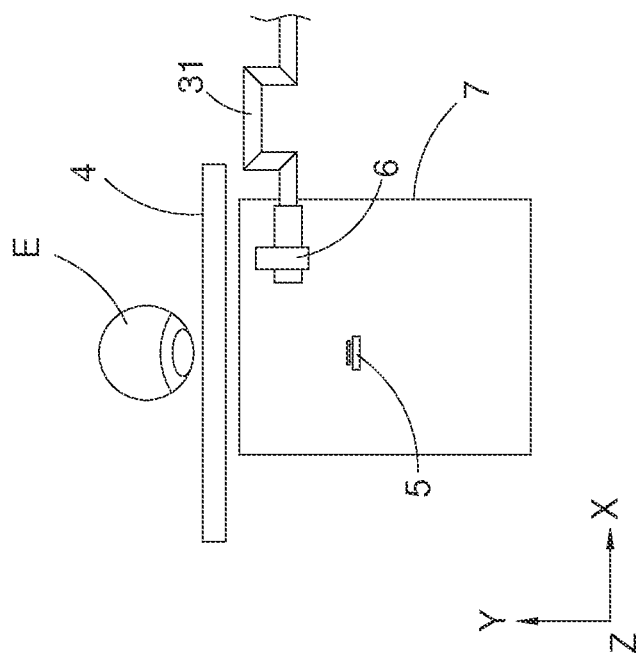
FIG. 4B is a second schematic view showing the movement of the positioning device and the laser beam projector of the ophthalmic laser apparatus relative to the patient's eye according to the embodiment of the present invention.

FIG. 4A and FIG. 4B show the movement of the positioning device 5 and the laser beam projector 6 of the ophthalmic laser apparatus 1 relative to the patient's eye E according to the embodiment of the present invention.

As shown in FIG. 4A, after the patient's head (eye E) is supported on the support bracket 4, the operating first moves the positioning device 5 by operating the moving stand 7 for positioning relative the position of the eye E (for example, the left eye or the right eye) of the patient supported on the support bracket 4. Next, after the positioning device 5 is positioned relative to the position of the patient's eye E, the operator moves the laser beam projector 6 based on the positioning result of the positioning device 5 to a position (primary positioning) aligned with the patient's eye E by operating the moving stand 7, as shown in FIG. 4B. After the laser beam projector 6 is moved to the position aligned with the patient's eye E by operating the moving stand 7, the eye tracking system 9 of the laser beam projector 6 will reposition relative to the position of the patient's eye E. According to the repositioning result of the eye tracking system 9, the position of the laser beam projector 6 is fine adjusted by the fine adjustment device 10, so that it is aligned with the patient's eye E (fine positioning) more accurately.

After the above-mentioned primary positioning and fine positioning, the laser beam projector 6 is accurately aligned with the patient's eye E. In this state, the laser beam L can be projected to the eye E of the patient through the laser beam projector 6.

It should be noted that while the laser beam projector 6 is moved to be aligned with the patient's eye E based on the positioning result of the positioning device 5, the positioning device 5 continuously acquires the position of the patient's eye E and the position of the laser beam projector 6.

Referring to FIG. 1 and FIG. 3, the ophthalmic laser apparatus 1 according to the present invention further includes a user interface 300 and a switch 400 connected to the controller 8. After the laser beam projector 6 is moved to a position precisely aligned with the eye E by operating the moving stand 7 and the fine adjustment device 10 of the laser beam projector 6, the operator can input the operating parameters of the ophthalmic laser apparatus 1 (for example, the operating parameters required for performing ophthalmic laser surgery) to the controller 8 through the user interface 300, and can operate the switch 400 to issue a command. This command is transmitted to the laser light source 2 through the controller 8, so that the laser light source 2 irradiates a corresponding laser beam L according to the operating parameters input through the user interface 300. Then, the laser beam L is transmitted to the laser beam projector 6 through the light guide module 30 and the light guide arm 31, and then is projected toward the eye E of the patient.

In the embodiment according to the present invention, as shown in FIG. 1, the user interface 300 includes a screen and a keyboard for the operator to input operating parameters and monitor the operation of the ophthalmic laser apparatus 1, for example, the primary positioning and fine positioning results of the laser beam projector 6. In addition, as shown in FIG. 1, the switch 400 is preferably a foot-operated switch. After operating the mobile stand 7 to move the laser beam projector 6 to be aligned with the eye E of the patient, the operator can operate the foot-operated switch to issue a command. The laser beam L irradiated from the laser light source 2 through the light guide module 30, the light guide arm 31 and the laser beam projector 6 is projected toward the eye E of the patient. However, those skilled in the art should understand that the present invention is not limited to the above-mentioned type of user interface 300 and switch 400, other types of user interfaces and switches may be used, as long as the above functions can be achieved.

FIG. 5 is a partial schematic view of the ophthalmic laser apparatus 1 according to the embodiment of the present invention when in use. It can be clearly seen in FIG. 5 that the patient's head is supported on the support bracket 4 so that the exposed surface of the eye E is perpendicular to the horizontal plane (XY plane).The laser beam projector 6 is precisely aligned with the patient's eye E through the positioning device 5 and the fine adjustment device 10. In this state, the laser beam L from the laser beam projector 6 is projected toward the patient's eye, thereby performing ophthalmic laser surgery. In other words, as shown in FIG. 5, the patient undergoes ophthalmic laser surgery in a sitting posture.

In summary, with the ophthalmic laser apparatus 1 of the present invention, since the support bracket 4 is configured to keep the exposed surface of the patient's eye E perpendicular to the horizontal plane (XY plane), that is, the patient is in a sitting posture. Therefore, in addition to related examinations before surgery in a sitting posture, the patient can receive the laser beam L projected from the laser beam projector 6 in a sitting posture for performing ophthalmic laser surgery. In this state, there will not be much difference in the condition of the patient's eyes (for example, the angle of rotation of the eye, etc.) when undergoing related examinations before surgery and when a laser beam is projected for ophthalmic laser surgery, so that the more precise operation of ophthalmic laser surgery can be performed. Therefore, the ophthalmic laser apparatus 1 according to the present invention can perform ophthalmic laser surgery under more precise conditions, and is particularly suitable for ophthalmic laser surgery that requires high precision.

In addition, with the ophthalmic laser apparatus 1 of the present invention, the alignment between the patient's eye E and the ophthalmic laser apparatus 1 is done by moving the laser beam projector 6 of the ophthalmic laser apparatus 1, instead of moving the patient relative to the ophthalmic laser apparatus 1. Therefore, there is no need for the operator (that is, the doctor or the surgical assistant) to move and adjust the operating table where the patient is located again and again during the surgery. It is only necessary to move the laser beam projector 6 to a position aligned with the patient's eye E by operating the moving stand 7. Therefore, the ophthalmic laser apparatus 1 according to the present invention is more convenient in operation and use.

On the other hand, there are psychological effects on patients who undergo ophthalmic laser surgery in a sitting or lying posture. Specifically, compared to the psychological pressure when a patient undergoes ophthalmic laser surgery on an operating table in a lying posture, the psychological pressure on the patient is relatively less because the ophthalmic laser apparatus 1 according to the present invention enables the patient to undergo ophthalmic laser surgery in the same sitting posture when examining the eyes. In other words, with the ophthalmic laser apparatus 1 according to the present invention, the patient can undergo ophthalmic laser surgery with a more relaxed attitude.

The accompanying drawings provided herein and referred to by the above description are for easy understanding of the disclosure. The drawings are only exemplificative and may be not made to scale, which means some features may be exaggerated while others may be understated. Thus, the drawings shall be deemed to be illustrative but not limiting.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. An ophthalmic laser apparatus, comprising:
   an excimer laser light source configured to generate an excimer laser beam;
   a light guide device configured to guide the excimer laser beam generated from the excimer laser light source;
   a support bracket configured to support a patient's head for an exposed surface of the patient's eye to be perpendicular to a horizontal plane;
   a positioning device configured to acquire a position of the patient's eye, said positioning device producing a positioning result corresponding to the position of the patient's eye;
   a laser beam projector, the laser beam projector being movable for alignment with the patient's eye based on the positioning result produced by the positioning device, wherein the excimer laser beam from the light guide device is projected toward the patient's eye through the laser beam projector for an ophthalmic procedure including Laser-Assisted In Situ Keratomileusis surgery, wherein the laser beam projector includes an eye tracking system and a fine adjustment device, the eye tracking system being configured to track the position of the patient's eye for generation of a repositioning result based on the patient's eye position, the fine adjustment device being operatively coupled to said eye tracking system and to said laser beam projector, wherein said fine adjustment device is configured to adjust a position of the laser beam projector relative to the patient's eye according to the repositioning result of the eye tracking system, thus accurately aligning the laser beam projector with the patient's eye;
   a moving stand, wherein the positioning device and the laser beam projector are disposed on the moving stand, the moving stand being configured to move the positioning device and the laser beam projector along an X direction, a Y direction, and/or a Z direction relative to the patient's eye; and
   a controller operatively coupled to the excimer laser light source and the laser beam projector to control the excimer laser light source to irradiate the excimer laser beam and to control the laser beam projector to project the excimer laser beam toward the patient's eye.

2. The ophthalmic laser apparatus as claimed in claim 1, wherein the controller is further operatively coupled to the eye tracking system and the fine adjustment device, said controller further controlling the fine adjustment device automatically to fine adjust the position of the laser beam projector according to the repositioning result of the eye tracking system.

3. The ophthalmic laser apparatus as claimed in claim 1, further comprising:
   a cabinet, the excimer laser light source and the controller being arranged on the cabinet, the cabinet being movable on the ground; and
   an operating platform disposed separately from the cabinet and displaceable relative to said cabinet, wherein the support bracket, the moving stand, the positioning device and the laser beam projector are positioned on the operating platform, the operating platform being movable on the ground;
   wherein the light guide device includes a light guide module and a light guide arm, wherein the light guide module is disposed on the cabinet, and the light guide arm is connected between the light guide module on the cabinet and the laser beam projector on the operating platform.

4. The ophthalmic laser apparatus as claimed in claim 1, wherein the positioning device acquires the position of the patient's eye, and said controller dynamically controls the position of the laser beam projector while the laser beam projector is moved to be aligned with the patient's eye.

5. The ophthalmic laser apparatus as claimed in claim 1, wherein the support bracket is adjustable in height along the Z direction.

6. The ophthalmic laser apparatus as claimed in claim 1, wherein the moving stand is operated manually so that the positioning device and the laser beam projector can move along the X direction, the Y direction and/or the Z direction.

7. The ophthalmic laser apparatus as claimed in claim 1, wherein the positioning device is a camera.

8. The ophthalmic laser apparatus as claimed in claim 1, further comprising a condenser, the condenser being arranged on one side of the laser beam projector, facing the patient's eye.

9. The ophthalmic laser apparatus as claimed in claim 1, further comprising:
   a user interface for input of operating parameters of the ophthalmic laser apparatus and for monitoring operation of the ophthalmic laser apparatus, the user interface being operatively connected to the controller, the operating parameters of the ophthalmic laser apparatus being submitted to the controller through the user interface; and
   a switch, said switch being operatively coupled to the controller and configured to issue a command in response to the input of the operating parameters, the command from said switch being transmitted to the excimer laser light source through the controller, resulting in irradiation of the excimer laser beam by the excimer laser light source according to the operating parameters.

10. The ophthalmic laser apparatus as claimed in claim 9, wherein the switch is a foot-operated switch.

* * * * *